United States Patent [19]
Yokota et al.

[11] Patent Number: 5,830,493
[45] Date of Patent: Nov. 3, 1998

[54] BONE-FORMING GRAFT

[75] Inventors: Shoji Yokota; Seitaro Shimokawa; Ritsu Sonohara; Akira Okada, all of Shizuoka; Koichiro Takahashi, Tokyo, all of Japan

[73] Assignee: Yamanouchi Pharmaceutical Co., Ltd., Tokyo, Japan

[21] Appl. No.: 817,409

[22] PCT Filed: Sep. 28, 1995

[86] PCT No.: PCT/JP95/01970

§ 371 Date: Mar. 25, 1997

§ 102(e) Date: Mar. 25, 1997

[87] PCT Pub. No.: WO96/10426

PCT Pub. Date: Apr. 11, 1996

[30] Foreign Application Priority Data

Sep. 30, 1994 [JP] Japan ................................. 6-261980

[51] Int. Cl.⁶ ....................................................... A61F 2/00
[52] U.S. Cl. .............................. 424/426; 623/12; 623/16; 523/115
[58] Field of Search .............................. 424/426; 623/12, 623/16; 523/115

[56] References Cited

U.S. PATENT DOCUMENTS

| | | |
|---|---|---|
| 4,713,076 | 12/1987 | Draenert . |
| 5,133,755 | 7/1992 | Brekke . |
| 5,520,923 | 5/1996 | Tjia et al. . |
| 5,665,114 | 9/1997 | Weadock et al. . |

FOREIGN PATENT DOCUMENTS

| | | |
|---|---|---|
| 3841397 | 12/1988 | Denmark . |
| 0277678 | 8/1988 | European Pat. Off. . |
| 63-238867 | 10/1988 | Japan . |
| 323864 | 1/1991 | Japan . |
| 2164024 | 5/1985 | United Kingdom . |

*Primary Examiner*—Thurman K. Page
*Assistant Examiner*—Brian K. Seidleck
*Attorney, Agent, or Firm*—Sughrue, Mion, Zinn, Macpeak & Seas, PLLC

[57] ABSTRACT

A bone-forming graft that includes a bone morphogenetic protein (BMP) carried on a composite porous body. The composite porous body has a porous frame of a bioabsorbable hydrophilic material and a surface layer of a bioabsorbable polymer material. In particular, the present invention relates to a bone-forming graft in which the bioabsorbable hydrophilic material is one or more compounds selected from a group consisting of gelatin, hyaluronic acid, a hyaluronic acid derivative, collagen, a collagen derivative, chitosan, a chitosan derivative, and triethanolamine alginate. The bioabsorbable polymeric material is one or more compounds selected from a group consisting of a polylactic acid, a copolymer of a polylactic acid and a polyglycolic acid, and a copolymer of poly[bis(p-carboxyphenoxy)propane]anhydride and sebacic acid. The graft has excellent formability and workability and has an internal structure suitable for in vivo bone formation. Bone formation occurs not only at the periphery of the graft but also within the graft.

13 Claims, 7 Drawing Sheets

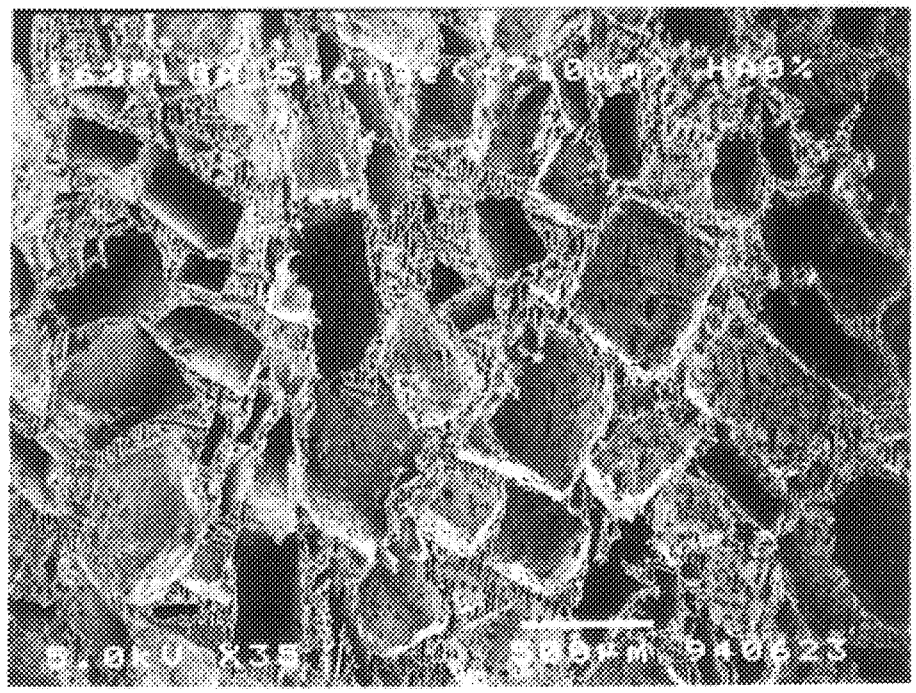
FIG. II

BONE-FORMING GRAFT

This application is a 35 USC 371 of PCT JP95/61970 filed Sep. 28, 1995.

1. Technical Field

The present invention relates to a bone-forming graft containing a bone morphogenetic protein, and a composite porous body which may be used as a carrier of the bone morphogenetic protein.

In particular, the present invention relates to a bone-forming graft which comprises a bone morphogenetic protein carried on a composite porous body, said composite porous body comprising a porous frame of a bioabsorbable hydrophilic material and a surface layer of a bioabsorbable polymer material; as well as to the composite porous body which is useful as a carrier for the bone morphogenetic protein.

2. Background Art

Bone morphogenetic protein (BMP) is an active protein which acts on the undifferentiated mesenchymal cells in the subcutaneous or muscle tissue to cause the differentiation thereof into chondroblasts or osteoblasts, and the formation of cartilage or bone. BMP was found in bovine demineralized bone matrix as a substance exhibiting ectopic bone inducing activity, but had not been purely isolated and therefore the concrete structure thereof had remained unknown. By the genetic engineering technique, however, the gene encoding the human BMP was cloned and the amino acid sequence thereof was elucidated. Further, it was found that the human BMP comprises a family of plural closely-related proteins having homologous amino acid sequences. Various types of recombinant human bone morphogenetic proteins (rhBMPs) were found [*Science*, vol. 242, pp. 1528–1534 (1988); *Proc. Natl. Acad. Sci. USA*, Vol. 87, pp 2220–2224 (1990); *Progress in Growth Factor Research*, Vol. 1, pp. 267–280 (1989); Japanese National-phase Publications No. 2-500241, No. 3-503649 and No. 3-505098; WO91/18098, WO92/05199, and WO93/09229]. Further, the rhBMPs were produced from transformants.

Even before the structure of the BMP was elucidated, various methods were proposed to use the BMP for treatment of damage, loss, or hypoplasia of bones or cartilage. Such proposals have been increased along with the production of recombinant BMP. When the BMP is used, it is extremely difficult to induce bone formation by locally implanting the BMP alone, and so the BMP is generally carried on a carrier and then the whole is locally implanted. The main purpose is not to disperse the BMP from the implanted site but to hold the BMP thereat at least for several days to several weeks, because the BMP requires such a period of time for local bone formation. The carrier is implanted in a living body together with the BMP as above, and thus requires low toxicity, low carcinogenicity, low antigenicity and so without affecting the BMP activity. Further, easy availability and, in some cases, biodegradability are desired.

Hitherto, for example, an implantable material wherein BMP is carried on a carrier of atelocollagen (Japanese Unexamined Patent Publication No. 62-89629), an implantable material prepared by impregnating a ceramics support with BMP and collagen carrier (Japanese Unexamined Patent Publication No. 60-253455), and a composition comprising rhBMP, a porous biodegradable polymer and the patient's blood (U.S. Pat. No. 5,171,579), or the like were proposed.

However, a graft composed of only BMP and a collagen carrier does not have sufficient formability nor strength. Further, such a graft quickly decomposes in the living body, and thus the shape cannot sufficiently be maintained or bone formation was not necessarily sufficient. If a non-decomposable or slowly decomposable substance (e.g., a ceramic material) is used as a support or such a substance is mixed with the carrier to improve the formability and cohesiveness in the living body, there is the problem that such a substance remains without being resorbed by the body, which inhibits formation of uniform bone tissues or there is a possibility that the remaining carrier causes bone resorption due to re-modeling of bone, etc. Furthermore, for the composition comprising porous biodegradable polymer particles and the patient's blood, an improvement was desired in terms of the workability and adjustability of shape at the time of surgery.

In addition, it is known that when a conventional graft comprising collagen or a biodegradable polymer is implanted in the living body, new bone is formed around the graft and then the bone forms gradually inside as well along with the decomposition of the graft. For example, an observation was reported that new bone was formed first in the portion around the graft and the bone formation was gradually spread into the inside of the graft in the case of a graft which contains an insoluble bone substrate or a collagen membrane as a carrier (*The Bone*, 1993, 12, Vol. 7, No. 4, pp. 97–104).

Further, Japanese Unexamined Patent Publication No. 1-232967 discloses a composition substituting for bone graft, in which polylactic acid (PLA) having voids which are connected to each other and filled with hyaluronic acid velour carrying an active substance such as BMP. However, neither particular production example nor test example thereof is described therein and thus its bone-forming capability is unknown. This technique differs from the present invention in that PLA serves as the skeleton maintaining the structure and has voids filled with a hyaluronic acid gel. This published patent application states that the "polylactic acid having voids which are connected to each other" forming the skeletal structure remains at least for 90 days after the transplantation and sustains its physical properties, which clearly indicates that it remains in the living body for a prolonged period of time. Because a PLA sponge was employed, the composition disclosed by this published patent application is rigid and fragile, it is poor in plasticity and elasticity and thus insufficient in formability and workability at implantation.

Furthermore, Japanese Unexamined Patent Publication 3-23864 discloses a collagen sponge having a polylactic acid system embedded therein which is useful as a filling for living tissue, while German Patent No. 3,841,397 discloses a sustained-release pharmaceutical carrier of a collagen sponge coated with polyester. However, there is no disclosure concerning applying BMP to such a carrier and employs as a bone-forming graft.

Accordingly, an object of the present invention is to provide a graft which has excellent formability and cohesiveness in the living body, has excellent workability at the time of surgery, and has an internal structure suitable for the formation of new bone.

DISCLOSURE OF THE INVENTION

In order to provide a graft which has excellent formability and cohesiveness in the living body, has excellent workability at the time of surgery, and has an internal structure suitable for the formation of new bone, the inventors made extensive studies. As a result, the present inventors found that a bone-forming graft which comprises a bone morphogenetic protein carried on a composite porous body, said composite porous body comprising a porous frame of a bioabsorbable hydrophilic material and a surface layer of a bioabsorbable polymer material, is capable of achieving the above objects, resulting in accomplishment of the present invention.

Further, the present invention also relates to a composite porous body which comprises a porous frame comprising a bioabsorbable hydrophilic material which is one or more compounds selected from a group consisting of gelatin, hyaluronic acid, and a hyaluronic acid derivative, and a bioabsorbable polymer material applied on the surface on the porous body, which is one or more compounds selected from a group consisting of a polylactic acid, a copolymer of a polylactic acid and a polyglycolic acid, and a copolymer of poly[bis(p-carboxyphenoxy)propane]anhydride and sebacic acid.

The present invention will be explained in detail hereinafter.

FIG. 1 schematically illustrates a partial section of a typical embodiment of the bone-forming graft of the present invention. That is, the bone-forming graft 1 of the present invention comprises (1) a composite porous body 4 comprising a porous frame 2 comprising a bioabsorbable hydrophilic material and a surface layer 3 comprising a bioabsorbable polymer material formed on the surface thereof and (2) a bone morphogenetic protein (BMP) 5 dispersively carried on the surface and inside of the composite porous body 4 (that is, in the porous frame 2 and/or the surface layer 3, and/or inside of the pores). A large number of pores 6 are contained in the bone-forming graft 1. These pores 6 have continuity and are opened to the outside. The partial cross-section shown in FIG. 1 is schematic, and thus the shape and size of each component are not limited to the illustrated embodiment.

The graft of the present invention is used mainly by being implanted at the site where the bone (including cartilage) is to be formed. If the graft of the present invention is implanted in the living body, the BMP acts at the implanted site to induce bone formation. The composite porous body functions as a delivery system which maintains the BMP at the local implantation site and thus form the bone in the desired shape, and at the same time the composite porous body per se is gradually resorbed in the living body and replaced by newly formed bone.

The bone morphogenetic protein (BMP) which may be used in the present invention and the method of preparation thereof are not limited, so long as the BMP is a protein which acts on undifferentiated mesenchymal cells to cause the differentiation thereof into chondroblasts or osteoblasts and the formation of cartilage or bone. Human BMP produced by genetic recombination technique, however, is preferable in terms of clinical safety, such as immunological safety or the like, and availability of a large amount of the material having stable quality. That is, the human BMP is a recombinant human bone morphogenetic protein (rhBMP) prepared by cultivating transformants (cells or microorganisms) containing a recombinant DNA including a base sequence encoding a human bone morphogenetic protein, and isolating and purifying the recombinant human bone morphogenetic protein produced by the transformants. As the human bone morphogenetic proteins (rhBMP), there may be mentioned, for example, rhBMP-2, rhBMP-3, rhBMP-4 (also known as rhBMP-2B), rhBMP-5, rhBMP-6, rhBMP-7, rhBMP-8, rhBMP-9, heterodimer of rhBMPs, or variants or defect variants thereof. The above protein can be used alone or in the form of a mixture thereof. rhBMP-2 is preferable.

The rhBMPs can be prepared by expressing in mammalian cells (for example, CHO), microorganisms (for example, $E.\ coil$), yeast, or the like. Mass production and isolation methods of rhBMP-2 are already established. Further, any other rhBMPs prepared and purified by the same manner may also be used [*Progress in Growth Factor Research*, Vol. 1, pp. 267–280 (1989)]. The known purified rhBMP-2 is a dimer protein having a molecular weight of about 30,000. Each monomer has a high mannose type saccharide chain at the $Asn^{56}$ residue [Abstract Sixth Interaction Symposium of the Protein Society, San Diego, Calif. (1992)].

The composite porous body constituting a support in the bone-forming graft according to the present invention comprises the porous frame and the surface layer as mentioned above. The porous frame has a porous structure as a base of the graft of the present invention. The concrete construction of the porous structure of the porous frame is not particularly limited, so long as the porous structure of the porous frame has a basic structure so that the graft prepared therefrom can form any porous structure, such as a sponge, net, fiber, or the like. Further, the surface layer is a layer applied at least at a part of the surface of the above porous frame and forms the composite porous body together with the porous frame. A preferable surface layer is a membrane uniformly applied over the entire surface of the porous frame along the porous structure of the frame. Further, the surface layer per se more preferably has a finer porous structure.

The bone-forming graft according to the present invention has the porous structure as above. Therefore, when the bone-forming graft of the present invention is implanted, blood and cells present in the living body quickly enter into the pores of the porous structure, a microenvironment suitable for bone formation is formed in the entire portions of the graft, that is, not only on the outer surface of, but also inside the pores in the graft, and further, the BMP carried on the surface of and/or in the pores in the graft is quickly released. Thereafter, the BMP carried in the porous frame in and/or the surface layer of the graft is gradually released along with the resorption of the porous frame and/or surface layer. Therefore, bone is formed not only on the surface of the graft, but also inside the pores of the graft and still further at the portions where the graft resorbed have existed.

As the bioabsorbable hydrophilic material, it is a substance which has biocompatibility (that is, is low in toxicity, shows only low foreign body reactions in the living body, and has a good affinity with the body tissue), bioabsorbability (that is, biodegradability), and hydrophilicity, but which has low solubility in water or is insoluble in water, and further has a solid shape at ambient temperature and formability. Any materials having these properties may be used without limitation. As illustrative bioabsorbable hydrophilic materials, there may be mentioned gelatin, hyaluronic acid, hyaluronic acid derivatives, such as, a polyionic complex of hyaluronic acid and chitosan, polyaminogalactosamine, alginic acid triethanolamine, gelatin, casein, keratin, collagen, myosin and/or fibroin (see, for example, Japanese Unexamined Patent Publication No. 6-73103), collagen, collagen derivatives, such as, succinylated collagen or methylated collagen, chitosan, chitosan derivatives, such as, methylpyrrolidone-chitosan, polyaminogalactosamine, triethanolamine alginate, casein, keratin, myosin, or fibroin. The bioabsorbable hydrophilic material is preferably a biosubstance, such as gelatin, hyaluronic acid, a hyaluronic acid derivative (in particular, a polyionic complex of gelatin and hyaluronic acid), collagen, a collagen derivative, chitosan, a chitosan derivative or a triethanolamine alginate, and more preferably gelatin, a polyionic complex of gelatin and hyaluronic acid, or collagen. The above bioabsorbable hydrophilic material can be used alone or in combination.

As the porous frame composed of the bioabsorbable hydrophilic material, any conventional porous material may be used. For example, as a gelatin porous material, it is preferable to use a porous material prepared by dissolving gelatin in water, foaming, and then freeze-drying to obtain a sponge. Particularly, a gelatin porous material with a pore size of about 50–500 µm, a density of 10–100 mg/ml and a porosity of not less than 90% [for example, Spongel (trade name: made by Yamanouchi Pharmaceutical Co., Ltd.)] is most preferable, because it can absorb more than about 30 times its weight of water, so is actually used as a hemostatic agent, and further, it is known that Spongel is easily resorbed in the tissue, and thus may be implanted in the living body and is a safe material with no antigenicity.

The collagen porous material used as the porous frame is preferably a porous material derived from atelocollagen of a low antigenicity formed into a sponge shape by a known method [for example, Helistat (trade name: Marion Laboratories, Inc.)]. Further, it is possible to use, as the porous material of a hyaluronic acid derivative, sponge composed of, for example, a gelatin/hyaluronic acid polyionic complex (Japanese Unexamined Patent Publication No. 6-73103); as a porous material of a hyaluronic acid, a hyaluronic acid porous material in which hyaluronic acid has been solidified and molded by a conventional method, and as a porous material of a chitosan derivative, a chitosan derivative described in *Carbohydrate Polymers*, 20, 99–106 (1993).

The porous frame may be of any shape (for example, a sponge, net, or fiber) and has a mean pore size of preferably 10–1,000 µm, more preferably 50–500 µm, and a porosity of preferably not less than 50%, more preferably not less than 70%, still more preferably not less than 90%.

The bioabsorbable polymer material of the present invention is a polymer which has biocompatibility (that is, has low toxicity, low foreign body reactions in the living body, and a good affinity with the body tissue), bioabsorbability (that is, biodegradability), and has a solid shape at ambient temperature and formability and further which has a certain strength. Illustrative examples of the bioabsorbable polymer material include a synthesized, biocompatible, biodegradable, bioabsorbable and hydrophobic polymer, for example, polylactic acid, a copolymer of a polylactic acid and a polyglycolic acid, a copolymer of poly[bis(p-carboxyphenoxy)propane]anhydride (PCPP) and sebacic acid [*J. Neurosurg.*, 80: 283–290 (1994)], or a polyhydroxybutyric acid (PHB), a polyhydroxypropionic acid (PHP), polymalic acid, or copolymers thereof, and the like. A polylactic acid, a copolymer of a polylactic acid and a polyglycolic acid, or a copolymer of poly[bis(p-carboxyphenoxy)propane]anhydride (PCPP) and sebacic acid is preferable. It is particularly preferable to use a polylactic acid having an average molecular weight of 5000–1,500,000, or a copolymer of a polylactic acid and a polyglycolic acid with an average molecular weight of 5000–1,500,000 and a polylactic acid/polyglycol ratio of at least 40%. The above bioabsorbable polymer materials can be used alone or in combination.

In order to form the surface layer of the bioabsorbable polymer material, a bioabsorbable polymer material dissolved in an appropriate solvent may be applied and dried on a surface and inside of the aforementioned porous frame. For example, the polylactic acid (PLA) or the copolymer of a polylactic acid and a polyglycolic acid (PLGA), particularly, a polylactic acid having an average molecular weight of 5000–1,500,000 or a copolymer of a polylactic acid and a polyglycolic acid having an average molecular weight of 5000–1,500,000 and a polylactic acid content (molar ratio) of at least 40%, is dissolved in an organic solvent in a concentration of 0.2–20% (w/w), preferable in a concentration of 1–16% (w/w), applying the resulting solution to the porous frame by any method which can form a layer composed of the bioabsorbable polymer material on the surface of the porous frame and on the surface of the inside pores (for example, by spraying or coating, preferably immersing) and then drying (for example, air drying or preferably freeze-drying) the layer. As the organic solvent for preparing the solution of the bioabsorbable polymer material, for example, dioxane, acetone, ethyl acetate, dimethylformamide, or glacial acetic acid may be used.

If desired, it is possible to optionally use other additives, for example, a gelling agent, a surfactant, a stabilizer and/or a pH adjusting agent, in order that BMP is more effectively carried on the composite porous body prepared from the porous frame and the surface layer by the above method, or the like.

As a gelling agent, there may be mentioned, for example, hyaluronic acid, carboxymethylcellulose (sodium), gelatin, collagen, a gelled polylactic acid/polyethyleneglycol copolymer or a patient's blood. One or more of the above agents may be added simultaneously with or after the addition of the BMP.

It is possible to add the surfactant to the porous frame and/or the surface layer, preferably to the surface layer of the bioabsorbable polymer material. The surfactant may be added to the surface layer simultaneously with or after applying of the bioabsorbable polymer material or the surfactant may be added to the surface layer by the washing treatment after applying of the bioabsorbable polymer material. The surfactant may be added to the porous frame simultaneously with preparing of the frame or before applying of surface layer. The surfactant is preferably a non-ionic surfactant, more preferably, a polyoxyethylenesorbitanalkylester, such as, Polysorbate 80, Polysorbate 20, or the like.

It is preferable to add the surfactant (particularly, Polysorbate 80) to the surface layer of the bioabsorbable polymer material, because the hydrophilicity and the absorption and invasion of blood and cells to the graft are improved. In these cases, a solution containing a surfactant in an amount of 0.01–10% by weight, preferable in an amount of 0.05–2% by weight, may be used to add to the surface of the surface layer or washing treatment may be carried out using the solution containing the surfactant.

It is possible to use as the stabilizer, for example, amino acids, such as glycine or a sugar, and as the pH adjusting agent, for example, a pharmaceutically acceptable organic or mineral acid such as citric acid. These agents may be added in the manner same as the above methods of adding the gelling agent and surfactant.

The composite porous body, which has a surface layer comprising a bioabsorbable polymer material on the surface of a porous frame comprising bioabsorbable hydrophilic material, has a mean pore size of preferably 10–1,000 µm, more preferably 40–600 µm, and a porosity of preferably not less than 40%, more preferably not less than 60%, most preferably not less than 80%.

The composite porous body maintains the porous structure in a certain period in a living body, allows invasion of cells, provides a place for bone forming, and is gradually decomposed and resorbed to finally disappear completely.

If necessary, the composite porous body of the present invention may be sterilized before applying BMP. As long as therapeutically acceptable, any sterilization methods may be employed, such as radioactive ray irradiation, ethylene oxide sterilization, and dry-heating sterilization.

In the bone-forming graft of the present invention, the BMP is carried on at least a portion of the composite porous body, i.e., on the surface, in the inside (in other words, in the porous frame and/or in the surface layer), and/or in the pores of the composite porous material, as explained above. In particular, the bioabsorbable hydrophilic material may effectively carry the BMP, because of a good absorbability of an aqueous solution of BMP and a good adsorbability of BMP. Although the bioabsorbable polymer material is hydrophobic, the absorbability and adsorptivity of BMP are improved when the surfactant is contained or the surface is treated with the surfactant. A gelling agent or the like may be added before or simultaneously with the addition of the BMP to improve the function to carry BMP on the surface of the composite porous body.

The method for carrying the BMP on the composite porous body of the present invention is not particularly limited, so long as it enables the BMP to be carried all over the composite porous body. Further, the BMP may be added at any stage of the production process of the composite porous body. For example, the BMP may be added during the production process of the porous frame, or may be added to the surface after the manufacture of the porous frame, or may be added simultaneously with applying the surface layer. Further, the BMP may be added when the composite porous body is treated with a gelling agent or surfactant.

The BMP may be added by soaking with the BMP solution. The resulting product may be used as it is as a graft, or the soaked material may be dried in a freeze-drier or the like. The dry graft may be used after wetted with water for injection or physiological saline solution upon use (implanting), or may directly be implanted as it is, which becomes quickly wetted with the blood.

The contents of the components per 1 ml of the bone-forming graft according to the present invention are not particularly limited. However, for example, the bioabsorbable hydrophilic material forming the porous frame is usually contained in an amount of not more than 500 mg, preferably not more than 300 mg, more preferably 5–100 mg; and the bioabsorbable polymer material forming the surface layer is contained usually in an amount of not more than 500 mg, preferably not more than 300 mg, more preferably 5–100 mg. The BMP may be contained in any concentration so long as the bone inducing function is achieved. When rhBMP-2 is used, however, the content is usually not less than 0.01 mg, preferably 0.01–20 mg, more preferably 0.1–5.0 mg.

An example of preferable embodiments of the bone-forming graft according to the present invention is as follows. When the composite porous body comprising the porous frame of a gelatin porous material and the surface layer of a copolymer of a polylactic acid and a polyglycolic acid (PLGA) is impregnated with an aqueous solution of BMP, a part of the BMP solution permeates through the micropores of the PLGA surface layer, and is adsorbed inside the PLGA and further inside the gelatin porous frame. The product may be dried by freeze-drying, if necessary. As a result, a bone-forming graft of the present invention in which BMP is carried all over the composite porous body can be obtained.

If the resulting bone-forming graft of the present invention is implanted in the living body, the BMP is released into the living body from the surface of the graft. Further, the internal BMP is also released gradually along with the resorption of the PLGA and the gelatin porous frame.

The graft of the present invention may be prepared at the time of application to carry BMP or may be stored after preparation to carry BMP under appropriate conditions until the time of application. The graft of the present invention may be implanted at the diseased site by methods known in the art to cure various types of bone or cartilage loss. That is, as the conventionally known graft, the graft of the present invention may be used in the living body and may be appropriately used in accordance with ordinary methods in the art in accordance with the object, application, application site, the state of the patient, etc.

The graft of the present invention substantially defines the shape of the bone newly formed as above. That is, bone formation occurs in accordance with the shape of the graft. Therefore, it is preferable to shape the graft of the present invention in accordance with the shape in which bone formation is desired. Further, the graft of the present invention does not require surgery for removal after the implantation surgery.

The various types of the grafts of the present invention may be used alone, or may also be used in any desired combination of plural members or plural kinds of the grafts. Further, the graft of the present invention may be used in combination with other known graft. When the fixing of the graft of the present invention to the site, the maintenance of the shape, or the strength is insufficient, other known reinforcing materials may be used at the same time. The reinforcing materials are, for example, a biocompatible film for affixing the graft, such as collagen films or Goretex films or polylactic acid films used in the GTR method, or fasteners between the graft of the present invention and the living tissue (particularly bone), such as metallic plates, bone-connecting pins, or fixing nails. If necessary, the reinforcing materials may be removed surgically after the bone formation. Further, the graft of the present invention may be used in combination with other known grafts.

Further, the present invention also relates to a composite porous body which comprises a porous frame comprising a bioabsorbable hydrophilic material which is one or more compounds selected from a group consisting of gelatin, hyaluronic acid, and a hyaluronic acid derivative, and a bioabsorbable polymer material applied on the surface on the porous frame, which is one or more compounds selected from a group consisting of a polylactic acid, a copolymer of a polylactic acid and a polyglycolic acid, and a copolymer of poly[bis(p-carboxyphenoxy)propane]anhydride and sebacic acid.

It is preferable to use a composite porous body which comprises, as the bioabsorbable hydrophilic material, one or more compounds selected from a group consisting of gelatin and a polyionic complex of gelatin and hyaluronic acid and, as the bioabsorbable polymer material, one or more compounds selected from a group consisting of polylactic acid having an average molecular weight of 5,000–1,500,000 and a copolymer of a polylactic acid and a polyglycolic acid having an average molecular weight of 5,000–1,500,000 and a polylactic acid content (molar ratio) of at least 40%. It is still preferable that a surfactant is further added to the surface layer of the composite porous body. It is particularly preferable to use a composite porous body comprising a gelatin sponge having a porous frame with a pore size of 50–500 $\mu$m and a porosity of at least 90%.

Industrial Applicability:

In the bone-forming graft according to the present invention, the porous frame and the surface layer respectively comprises the bioabsorbable hydrophilic material and the bioabsorbable polymer material. It is known that each of these materials may be used as a carrier for BMP, respectively. However, there arises a problem that a bioabsorbable hydrophilic material such as gelatin or collagen is flexible and thus easily deformed. Also, such a material is quickly decomposed in the living body and resorbed within 1 to 2 weeks. Thus, it is impossible to obtain a graft capable of maintaining its shape for a certain period of time in the living body, and it is sometimes difficult to obtain a bone with the desired shape. On the other hand, a bioabsorbable polymer material is inferior in the function to carry BMP because of its hydrophobic nature. Further, though the bioabsorbable polymer material has biocompatibility, it is weaker than that of collagen or the like. Although the bioabsorbable polymer material has a certain degree of hardness, it is poor in plasticity and is fragile, thus showing only insufficient formability. In addition, it is fragile and liable to be broken in a humid state after the implantation.

From these points, it easily occurs to us that a carrier having sufficient biocompatibility and strength may be obtained by coating a bioabsorbable polymer material formed in a porous form with a material having excellent biocompatibility such as collagen. In practice, however, such a carrier is not a satisfactory one, since it has poor plasticity and is fragile, thus showing insufficient formability and workability.

The present inventors have found that the bone-forming graft of the present invention, in which BMP is carried on a composite porous body comprising a gelatin sponge or the like coated with a bioabsorbable hydrophilic material having poor biocompatibility, is unexpectedly excellent in biocompatibility and hydrophilic nature and also has good function to carry BMP. Different from a polymer material coated with collagen or the like, furthermore, the graft of the present invention has good elasticity and excellent workability and suitability in operation. Moreover, it was found that the graft of the present invention shows quick and good bone-formation not only around the graft but also the inside of it, which indicates it has a good ability to form bone.

Namely, the bone-forming graft of the present invention has excellent characteristics as will be shown below which are never observed in the conventional grafts carrying BMP.

The bone-forming graft of the present invention is a flexible carrier with appropriate elasticity. Thus, it is easy to shape, is not fragilely breakable, and can be shaped into any form. Further, it can be shaped into a sheet and wrapped, can fill in a hole of predetermined shape, and easily fits for the shape of a missing site of bone. Namely, it is excellent in workability and suitability.

The bone-forming graft of the present invention has appropriate strength and elasticity. Thus, it can retain a certain shape over a long period of time during storage outside the living body or for the necessary period of time after implantation in the living body. As a result, the space required for bone formation can be held and thus bone of the desired shape can be formed. Further, the bone-forming graft of the present invention has excellent hydrophilicity and an excellent property to allow body fluids (cells, blood, or the like) to penetrate into all over the graft. Furthermore, its porous state is stably maintained for a certain period of time after implantation. Therefore, it is possible to provide stable microenvironment necessary for the growth of bone cells. It has excellent adsorbability of BMP, has an excellent function to carry BMP and can gradually release BMP in the living body. It can prevent BMP from leakage from the carrier. Accordingly, the bone thus formed has the same shape as that of the graft. In addition, it is resorbed and replaced in the living body by newly formed bone after a certain period of time as the bone formation proceeds. Therefore, the graft per se does not remain over a prolonged time in the living body, which allows the formation of a good bone tissue. Moreover, it scarcely irritates the transplantation site and shows no formation of hematocyst or the like, which is observed in the case of PLGA carriers.

The graft of the present invention is almost completely resorbed in the living body within about 3 to 12 weeks, though the absorption rate varies depending on the size, shape, application site, polymer type, concentration, etc.

Because of these properties, the graft of the present invention makes it possible to form good new bone. Namely, as will be shown in the following Test Examples, it was confirmed that the new bone formation with the use of the graft of the present invention is observed at the early stage not only around the graft but also the inside thereof. This fact suggests that the graft of the present invention has good environment suitable for bone formation also in its internal part.

As described above, the composite porous body of the present invention is excellent in biocompatibility, in hydrophilicity and in carrying active substances such as BMP. Furthermore, it is a flexible carrier with appropriate elasticity, is easy to shape, is not fragilely breakable, and can be shaped into any form. Further, it can be shaped into a sheet and wrapped, can fill in a hole of predetermined shape, and fits for the shape of a bone-missing part, thus being excellent in workability and suitability.

The composite porous body of the present invention can retain a certain shape and strength over a long period of time during storage outside the living body but for the necessary period of time after implantation in the living body. In addition, it is gradually resorbed by the living body after a certain period of time and does not remain over a prolonged time in the living body. Moreover, it scarcely irritates the transplantation site and, therefore, is useful as a biocompatible material.

Accordingly, it is useful as a sustained-release carrier for active substances such as polypeptides, a temporary substitute for living tissues such as bone and cartilage, or a carrier of grafts for forming living tissues such as bone and cartilage. In particular, it is useful as the above-mentioned bone-forming graft carrying BMP.

The following tests and results are shown to prove excellent effects of the bone-forming graft of the present invention.

Implantation Test Example 1

(1) Procedure

The grafts of the present invention were subcutaneously implanted at the left and right thoracic regions of male rats (5 weeks old: Long Evans) anesthetized with ether, and the ectopic bone formation activity was evaluated (n=6 to 8). The following grafts were used:

(A) a graft prepared from a gelatin sponge in which a solution containing 2% by weight of an D, L-lactic acid/glycolic acid copolymer was soaked in Example 1 [hereinafter referred to as the graft (A)], (B) a graft prepared from a gelatin sponge in which a solution containing 4% by weight of an D, L-lactic acid/glycolic acid copolymer was soaked in Example 1 [hereinafter referred to as the graft (B)], and (C) a graft prepared from a gelatin sponge in which a solution containing 4% by weight of an D, L-lactic acid/glycolic acid copolymer was soaked in Example 2 [hereinafter referred to as the graft (C)]. The above grafts (A), (B) and (C) respectively containing about 20 μg/100 μl or about 80 μg/100 μl of rhBMP-2 were used as the graft of the present invention. As control groups, the grafts (A), (B) and (C) not containing rhBMP-2 were prepared and implanted as above. The graft was explanted at 1, 2, 3 and 4 weeks after the implantation. The explanted tissue was examined as to calcium content (atomic absorption spectrophotometry), Soft X-ray photograph, pQCT (peripheral quantitative computed tomography), and histological observation to evaluate the degree of bone formation.

(2) Results of calcium content (atomic absorption spectrophotometry)

The explanted tissue was immersed in 2N hydrochloric acid for at least 2 days to extract the calcium. The calcium content was measured by the atomic absorption spectrophotometry.

Time course of the calcium content in the explanted tissue is shown in FIG. 2. In the control groups with no rhBMP-2 (shown by 0 μg in FIG. 2), almost no calcium was detected at all in any case of the grafts (A), (B), and (C), whereas in the groups containing 20 μg/100 μl of rhBMP-2 (shown by 20 μg in FIG. 2) and the group containing 80 μg/100 μl of rhBMP-2 (shown by 80 μg in FIG. 2), the calcium content was increased with time from 1 week after the implantation in each of the grafts (A), (B), and (C) and reached maximum values at 3 weeks or 4 weeks after the implantation in almost all the groups. Further, the values were largely dependent on the dose of the rhBMP-2. In FIG. 2, "wk" means the elapse of time (weeks) after implantation.

(3) Soft X-ray observations

According to the Soft X-ray photographs of the explanted tissue, in the control groups not containing rhBMP-2, only weak radiopacity as that of a soft tissue was observed in all the weeks examined. No formation of osseous tissue was observed. It is believed that the above weak radiopacity is caused by the graft. Since it shrank with time, it is suggested that the graft is gradually resorbed. Further, since the radiopacity was observed even at 4 weeks after the implantation, it is suggested that a part of the graft remains even at 4 weeks.

In the groups containing rhBMP-2 in an amount of 20 μg/100 μl, the radiopacity caused by the induced osseous tissue induced at 1 week after the implantation was observed. The radiopacity became more remarkable from 2 weeks after the implantation. The Soft X-ray photographs at 3 weeks after the implantation are shown in FIG. 3 [graft (A) containing rhBMP-2 in an amount of 20 μg/100 μl], FIG. 4 (graft (B) containing rhBMP-2 in an amount of 20 μg/100 μl), and FIG. 5 (graft (C) containing rhBMP-2 in an amount of 20 μg/100 μl).

It is suggested from the above Soft X-ray photographs that osseous tissue was formed substantially along with the shape of the graft.

(4) Results of examination as to calcium distribution by PQCT

PQCT was used to examine the calcium distribution of the explanted tissue. The results of the examination as to the calcium distribution in the vertical cross-section of the explanted tissue show that a spotty calcium distribution was observed not only at the surface layer portion of the graft, but also at the inside of the graft. It was suggested that osseous tissue was formed along the pore portions of the graft.

(5) Results of histological observation

The explanted tissue was decalcified with formic acid and citric acid, then embedded in paraffin and cut into thin slices. The slices were stained with hematoxylin and eosin (HE) and examined under an optical microscope. The tissues of the graft (C) (group containing 20 μg/100 μl of rhBMP-2) at 3 weeks after the implantation are shown in FIGS. 6 to 8. FIG. 6 shows a section (80×) obtained by cutting the center of the explanted tissue in the vertical direction, while FIG. 7 shows a section (66×) obtained by cutting the explanted tissue in the horizontal direction. In both cases, the osseous tissue stained red with HE (black portions in FIGS. 6 and 7) was observed all over the graft. Osseous tissue was formed up to the inside of the graft along the pores of the graft. FIG. 8 is a higher magnification of FIG. 7 (300×), which shows myeloid tissue composed of blood capillaries, bone marrow cells, and adipose tissue between the bone matrix. Further, the remaining of the graft was observed with time. As a result, the porous graft substantially remained, but some of the gelatin began to be resorbed at 1 week after the implantation. At 2 weeks after the implantation, the resorption of the gelatin was further advanced. At 3 weeks after the implantation, almost all of the gelatin was resorbed.

On the other hand, the PLGA remained inside the graft as a thin layer. A colorless, transparent and thin layer lining the large and small pores was observed even at 4 weeks after the implantation.

Further, bleeding, necrosis, edema, or other changes were not observed in the tissue surrounding the graft of the present invention. This showed that the graft had only a weak local irritation.

(6) Discussion

From the above results, it was confirmed in a rat ectopic bone formation assay that the graft of the present invention has an excellent bone formation activity which maximizes the bone formation by the rhBMP-2 even at 3 weeks or more after the implantation and, further, can induce an excellent osseous tissue even inside the graft. It was also confirmed that the graft of this invention is gradually resorbed and shrinks in the living body, and has a low local irritation.

Implantation Test Example 2

(1) Test procedure

The procedure of the above Implantation Test Example 1 was repeated except using, as the bone-forming graft of the present invention, the porous graft produced in Example 23 containing 0.1 mg/ml or 0.4 mg/ml of rhBMP-2. As controls, the following grafts also containing 0.1 mg/ml or 0.4 mg/ml of rhBMP were prepared and implanted.

Comparative graft A: a graft prepared by adding porous microspheres of PLGA prepared by the method described in U.S. Pat. No. 5,171,579 (average particle size: about 250 μm, average pore size: about 30 μm) to a mixture of an rhBMP-2 solution with blood (1:9) and solidifying it into a paste.

Comparative graft B: a graft prepared by dropping a mixture of an rhBMP-2 solution with blood (1:9) to a PLGA sponge (pore size: 100–500 μm, porosity: 90%), prepared by adding sodium chloride granules to dioxane containing 16% by weight of PLGA (molar ratio=50:50, molecular weight: 40,000, made by Boehringer Mannheim), freeze-drying, washing with water to thereby eliminate the sodium chloride via dissolution, and drying, so as to make the sponge to absorb the rhBMP/blood mixture.

FIG. 9 is an electron micrography of the graft of the present invention not containing BMP, i.e., the composite porous body, while FIGS. 10 and 11 are electron micrographies of the carriers respectively with the use of the comparative grafts A and B not containing BMP.

The graft was explanted at 1, 2, 3 and 4 weeks after the implantation. The explanted tissue was examined as to determine the wet weight and calcium content (atomic absorption spectrophotometry) followed by histological observation to evaluate the degree of bone formation.

(2) Results

The comparison of carriers under the electron microscope indicated that the composite porous body employed in the graft of the present invention had a structure with a number of connected pores and thus exhibited an excellent property to allow body fluids and cells to penetrate thereinto.

As the result of the Implantation Test, the comparative graft A showed good bone formation but sero-sanguineous formation at the center part and swelling were observed. The comparative graft B had only insufficient strength at implanting and fragile. Namely, it was poor in workability. After the implantation, further, the carrier was divided due to the insufficient strength and sero-sanguineous formation and swelling were observed. In contrast, the graft of the present invention was excellent in flexibility and workability at the implantation. After the implantation, a osseous tissue which was almost the same as the graft in shape and size was induced while showing almost no sero-sanguineous formation or swelling. The explanted tissue showed a calcium content/wet weight ratio higher than those of other carriers.

Implantation Test Example 3

(1) Procedure

To evaluate the bone forming ability in a bony defect site, full thickness defect (1.5 cm in length) was created at the right ulna of Japanese white rabbits (aged 16 to 20 weeks, male) under anesthesia. As the graft of the present invention, a graft containing about 0.1 mg/ml or 0.4 mg/ml of rhBMP-2 in a composite porous body prepared by allowing the gelatin sponge to absorb a solution containing 4% by weight of D,L-lactic acid/glycolic acid copolymer (see Example 3) was implanted into the defect site. After the implantation, radiography and cross-sectional observation with pQCT were simultaneously performed on the defect site with time to thereby observe the calcium distribution. After 12 weeks, the animals were sacrificed. After fixation with formalin and decalcification, paraffin-embedded slices were prepared and histologically examined.

(2) Results

When deformed, the graft of the present invention showed excellent restoration and it could be easily embedded into the body defect site, thus showing good workability. Two weeks after the implantation, radiopacity was observed and bony union between separated stump was observed after 3 to 4 weeks. PQCT observation indicated that bone formation proceeded toward the center of the carrier within 3 to 6 weeks after the implantation and then the center part of newly formed bone was resorbed again. These findings seemingly suggest the formation of cortical bone and marrow cavity in association with re-modeling. The formation of bone with this structure was also observed histologically. The union rate speed and the amount of the bone thus formed depended on the dose of rhBMP-2.

4. BMP adsorption per unit graft volume and adsorption ratio (1) Procedure

Various carriers of 10×10×5 mm in size [the composite porous body prepared by allowing a gelatin sponge to absorb a solution containing 4% by weight of D,L-lactic acid/glycolic acid copolymer prepared in Example 3; a PLA sponge (product name: DRILAC CUBE, made by THM BIOMEDICAL INC.); and a gelatin sponge (product name: SPONGEL, made by Yamanouchi Pharmaceutical Co., Ltd.)] were wetted by adding dropwise a 0.4 mg/ml solution of $^{125}$I-rhBMP-2 until the carriers could not absorb any more. After allowing to stand at room temperature for 60 minutes, the various carriers containing rhBMP-2 were each introduced into a 5 ml syringe provided with a stainless mesh (150 $\mu$m) at the bottom. Then the syringe was inserted into a 14 ml polypropylene centrifuge tube and centrifuged at 2,500 rpm for 20 minutes (in the case of the gelatin sponge, at 2,000 rpm for 10 minutes). Then the radioactivity of the carrier was measured and the ratio to the starting radioactivity was determined.

(2) Results

The graft of the present invention showed the largest BMP adsorption per unit volume, i.e., about 1.5 times as much as those of the PLA sponge and gelatin sponge. Also, its adsorption ratio to the total (about 70%) was higher than those of the PLA sponge (50%) and gelatin sponge (60%).

As shown above, the graft of the present invention rapidly induces bone formation in the living body, is gradually replaced as a whole by newly formed bone, does not remain at all, enables to form good osseous tissue, and further has excellent workability and shape-adjustability upon application. Accordingly, the graft of the present invention may be applied to diseased sites by methods known in the art so as to restore various loss of bone or cartilage caused by trauma, disease, ectrogency, or the like. The graft of the present invention exhibits low inflammatory and excellent biocompatibility when implanted in the living body. Further, bone or cartilage can be restored in a close state to nature The graft of the present invention can be applied to various fields, for example, the restoration of loss of bone or cartilage caused by trauma such as fractures, diseases such as tumors or inflammatory, degenerative, or necrotic bone diseases, bone harvest accompanying surgery such as brain surgery or orthopedic surgery, or the like, the promotion of healing of various fractures, bone formation around artificial implants such as artificial joints, artificial bone, or artificial radix dentis, the prosthesis of bone in orthopedic surgery, such as the promotion of binding at the time of use of artificial implants, the promotion of spinal fusion, or leg extension, the prosthesis of bone or cartilage in plastic surgery, such as regeneration of cartilage or rebuilding of joints, the restoration of bone, cartilage, or cementum in the dental field, and the augmentation of bone for implant use.

BRIEF DESCRIPTION OF DRAWINGS

Explanation of References 1. graft; 2. porous frame, 3. surface layer, 4. composite porous body, 5. BMP; 6. pore

FIG. 11 is a electron micrograph (35×) of the carrier used for the comparative graft B. Best Mode for Carrying out the Invention The present invention now will be further illustrated by, but by no means limited to, the following Examples.

EXAMPLE 1

Figure 1:
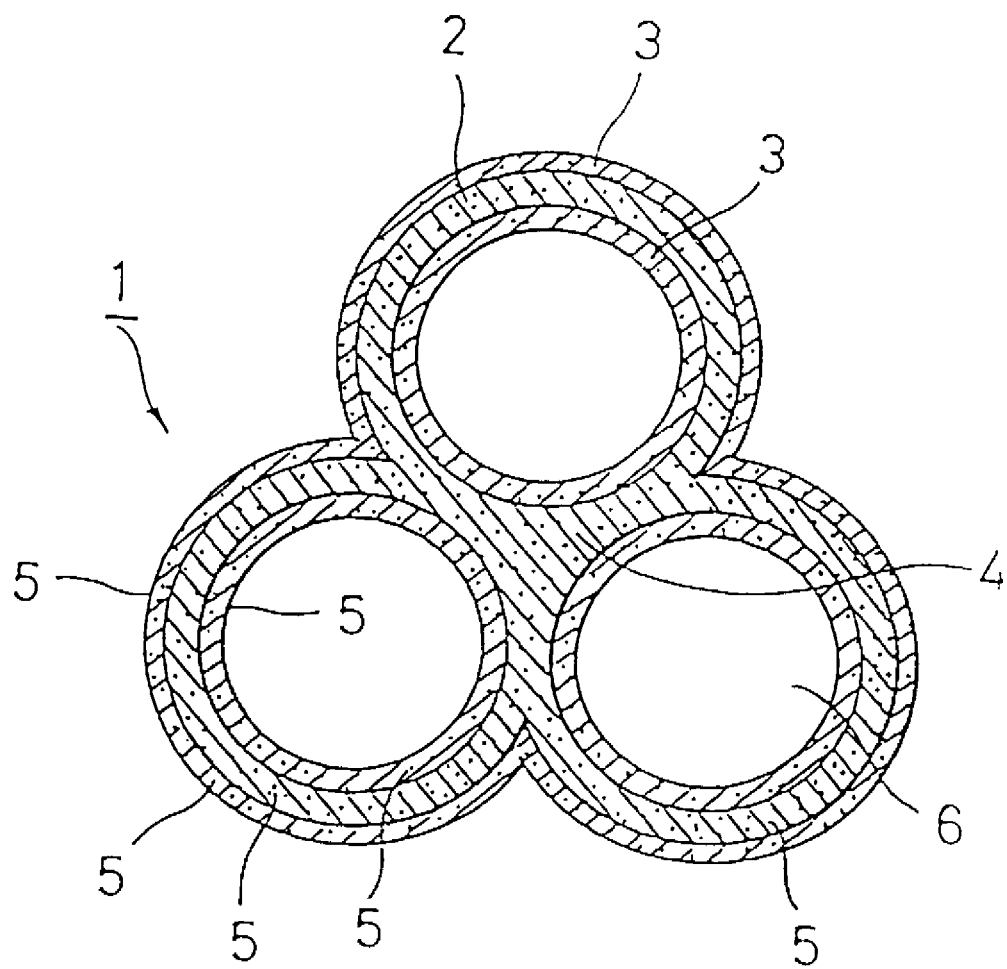
FIG. 1 is an explanatory view showing schematically a partial sectional structure of a representative embodiment of the graft of the present invention.
Figure 2:
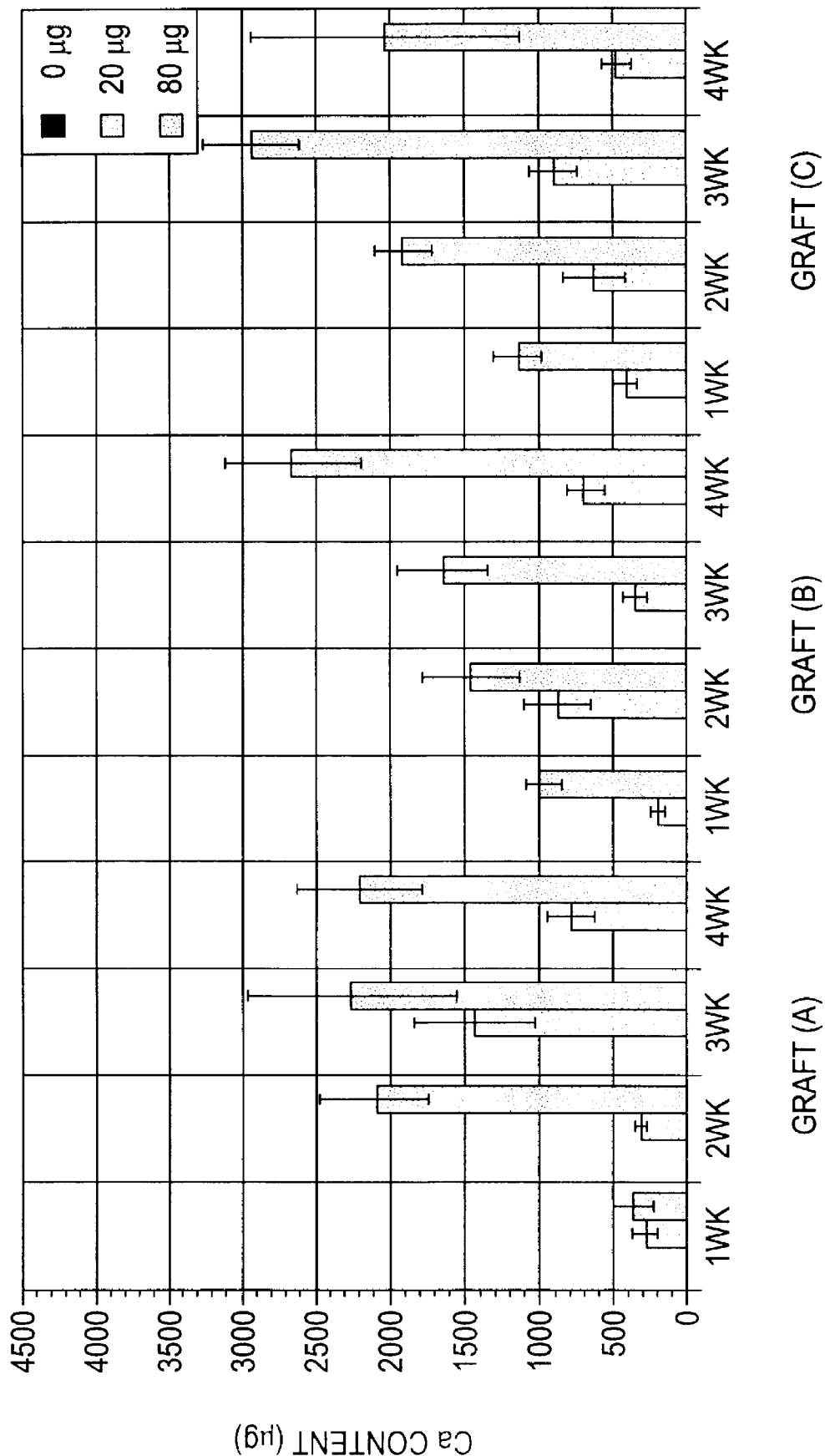
FIG. 2 is a graph showing time course of the calcium content when the graft of the present invention was implanted.
Figure 3:
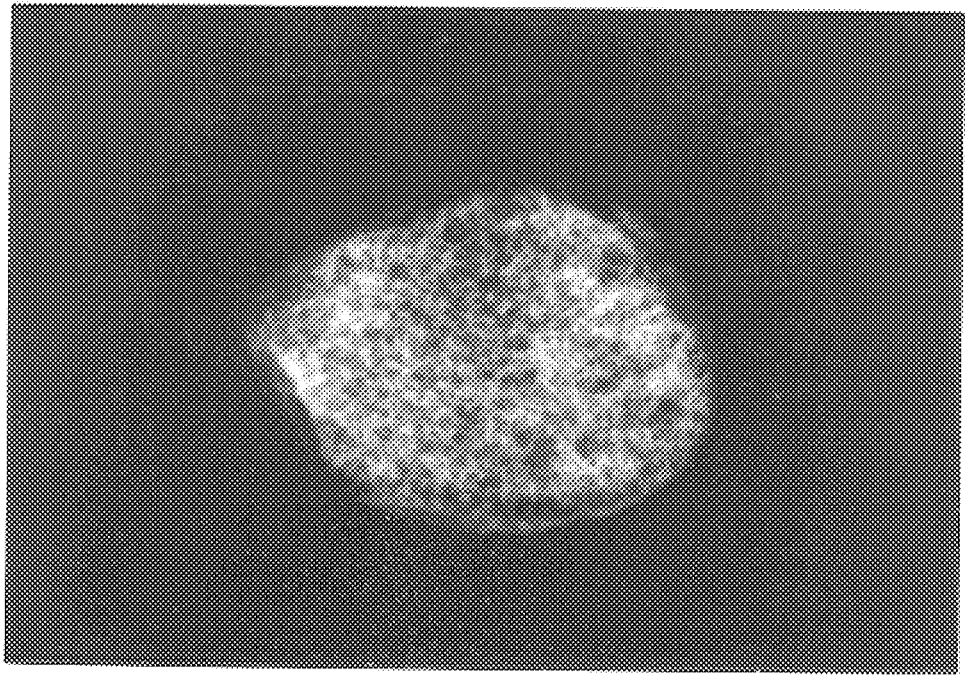
FIG. 3 is a Soft X-ray photograph at 3 weeks after the implantation of the present graft (A) containing rhBMP-2 in an amount of 20 $\mu$g/100 $\mu$l.
Figure 4:
FIG. 4 is a Soft X-ray photograph at 3 weeks after the implantation of the present graft (B) containing rhBMP-2 in an amount of 20 $\mu$g/100 $\mu$l.
Figure 5:
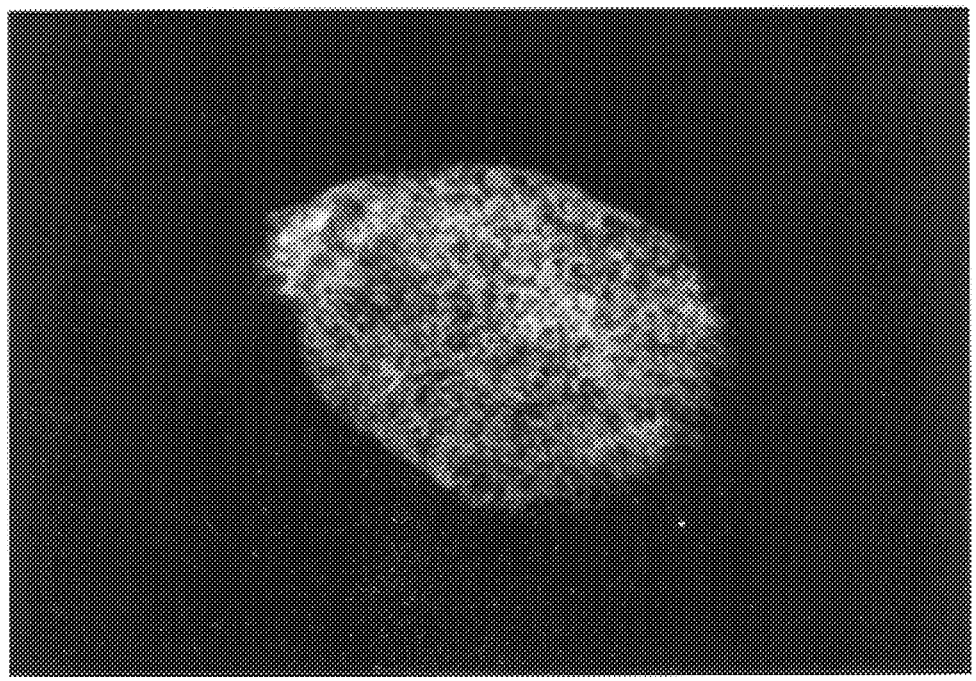
FIG. 5 is a Soft X-ray photograph at 3 weeks after the implantation of the present graft (C) containing rhBMP-2 in an amount of 20 $\mu$g/100 $\mu$l.
Figure 6:
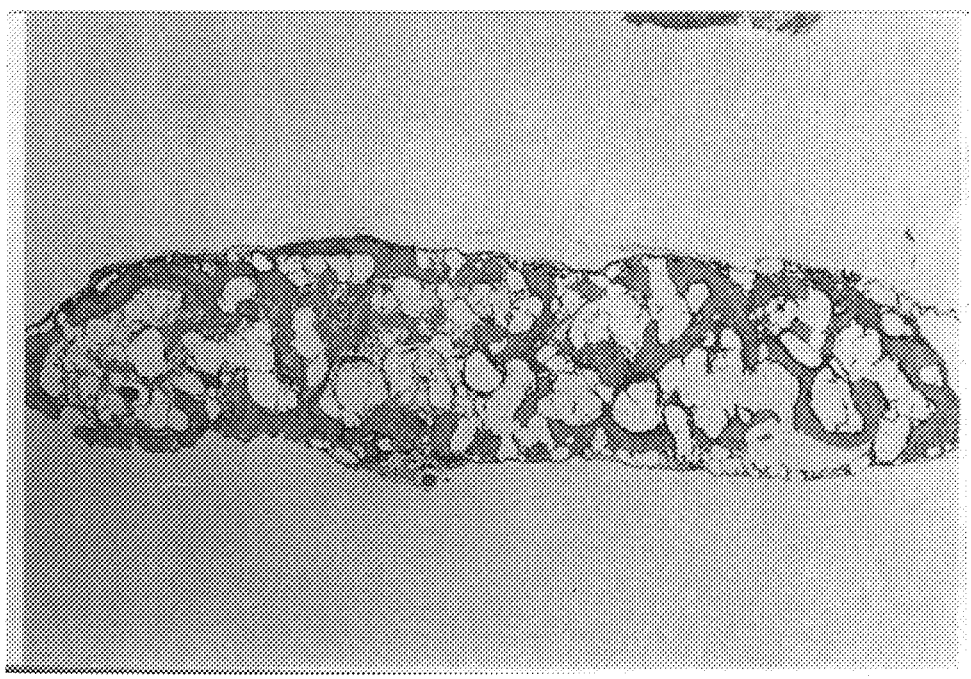
FIG. 6 is a section (80×) obtained by cutting in the vertical direction the explanted tissue of the present graft (C) containing rhBMP-2 in an amount of 20 $\mu$g/100 $\mu$l.
Figure 7:
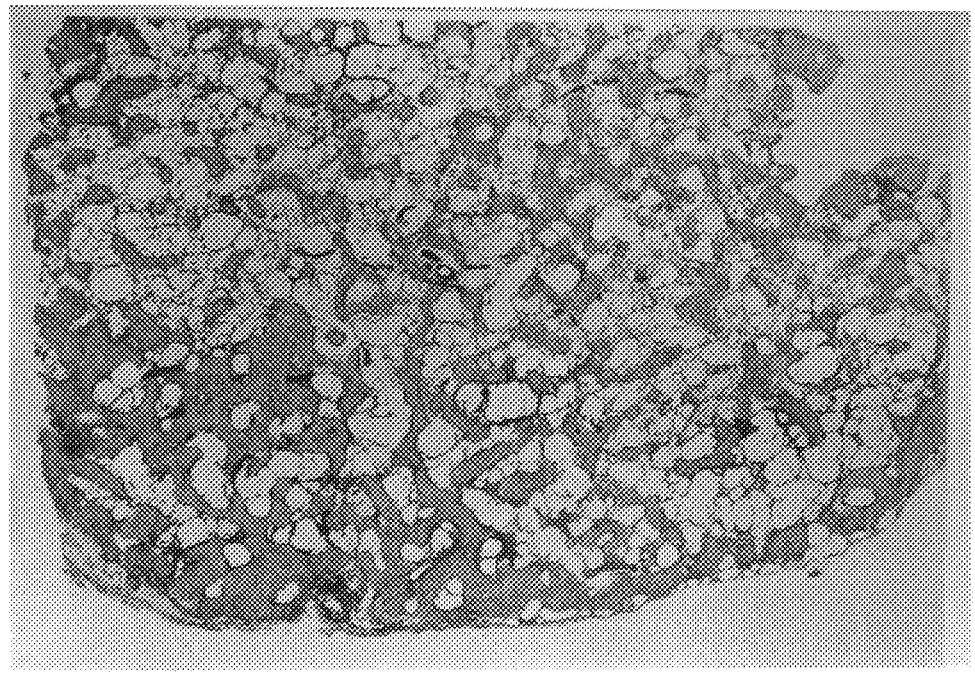
FIG. 7 is a section (66×) obtained by cutting in the horizontal direction the explanted tissue of the present graft (C) containing rhBMP-2 in an amount of 20 $\mu$g/100 $\mu$l.
Figure 8:
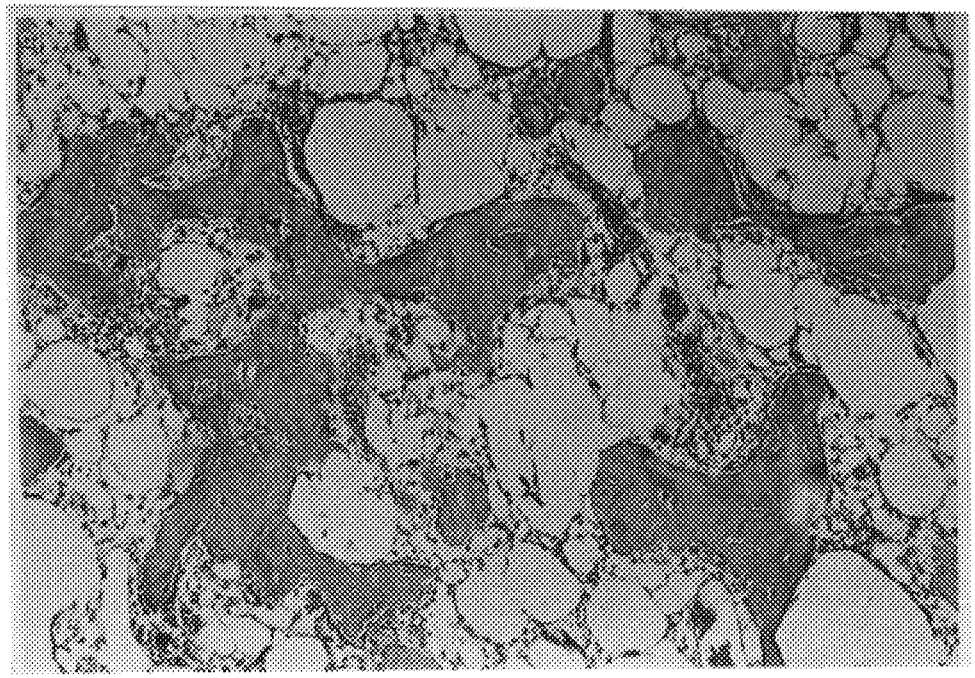
FIG. 8 is a higher magnification (330×) of FIG. 7
Figure 9:
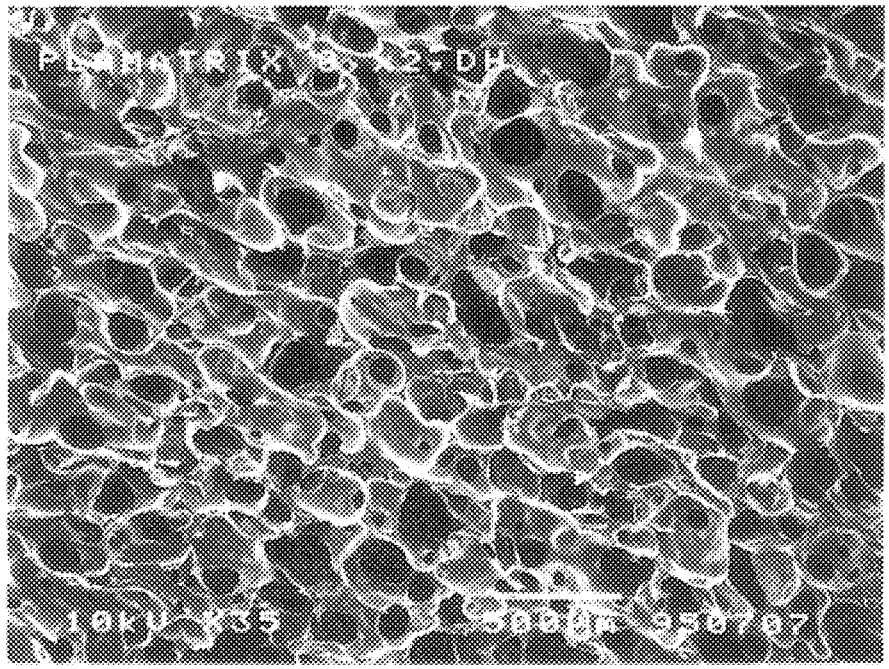
FIG. 9 is a electron micrograph (35×) of the composite porous body of the present invention.
Figure 10:
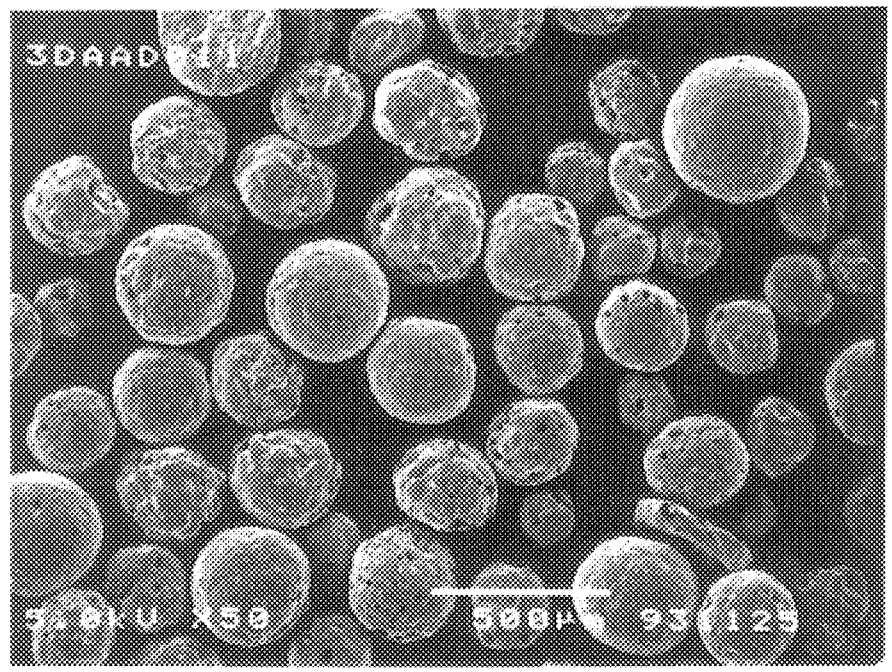
FIG. 10 is a electron micrograph (50×) of the carrier used for the comparative graft A.

A copolymer (2.0 g or 4.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 (reagent grade; made by Kanto Chemical) had been added in advance to 0.1% by weight, and dissolved under heat to obtain 100 ml of a polymer solution. The polymer solution was cooled to room temperature. Thereafter, a hemostatic gelatin sponge (trade name=Spongel; made by Yamanouchi Pharmaceutical Co., Ltd.) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. After the freeze-dried sponge was cut into a piece of 7 mm×7 mm×4 mm, about 200 μl of a solution prepared by mixing a solution of rhBMP-2 [made by Genetics Institute (also used in the following Examples)] [2 mg/ml to 8 mg/ml; 2.5% glycine, 0.5% sucrose, 5 mM sodium chloride, 5 mM glutamic acid, 0.01% Polysorbate 80; pH 4.5] and blood in a ratio of 1:9 was added dropwise whereby the solution was absorbed to obtain porous bone-forming grafts of the present invention containing rhBMP-2 (20 μg/100 μl to 80 μg/100 μl).

EXAMPLE 2

A copolymer (2.0 g or 4.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. After the freeze-dried sponge was wetted by adding dropwise a solution containing 0.25% by weight of sodium hyaluronate from chicken combs (made by Wako Pure Chemicals), the wetted sponge was freeze-dried by a known method. Further, the freeze-dried sponge was cut into a piece of 7 mm×7 mm×4 mm, and then, about 200 μl of a solution prepared by mixing a solution of rhBMP-2 [2 mg/ml to 8 mg/ml; 2.5% glycine, 0.5% sucrose, 5 mM sodium chloride, 5 mM glutamic acid, 0.01% Polysorbate 80; pH 4.5] and blood in a ratio of 1:9 was added dropwise whereby the solution was absorbed to obtain porous bone-forming grafts of the present invention containing rhBMP-2 (20 μg/100 μl to 80 μg/100 μl).

EXAMPLE 3

A copolymer (2.0 g or 4.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. Then, about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] was added dropwise whereby the solution was absorbed to obtain porous bone-forming grafts of the present invention.

EXAMPLE 4

A copolymer (2.0 g or 4.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 5

A copolymer (2.0 g or 4.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise an aqueous solution of 0.2% gelatin (reagent grade; made by Biorad), and then, freeze-dried by a known method. Further, the freeze-dried sponge was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed to obtain porous bone-forming grafts of the present invention.

EXAMPLE 6

A copolymer (2.0 g or 4.0 g) of D,L-lactic acid and glycolic acid (molar ratio=50:50, molecular weight=40,000;

made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise about 70 ml of a solution containing 0.2% gelatin (reagent grade; made by Biorad) and rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 7

A copolymer (2.0 g or 4.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise about 70 ml of a solution containing 0.2% by weight of sodium hyaluronate from chicken combs (made by Wako Pure Chemicals) and rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 8

A copolymer (2.0 g or 4.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise an aqueous solution of 0.2% sodium hyaluronate from chicken combs (made by Wako Pure Chemicals), and then, freeze-dried by a known method. Further, the freeze-dried sponge was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed to obtain porous bone-forming grafts of the present invention.

EXAMPLE 9

A copolymer (2.0 g or 4.0 g) of D,L-lactic acid and glycolic acid (molar ratio=50:50, molecular weight=40,000; made by Boehringer-Ingelheim) was added to glacial acetic acid (reagent grade; made by Kanto Chemical) in which Polysorbate 80 had been added in advance to 0.1% by weight, and dissolved to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar. The freeze-dried sponge was immersed twice in 200 ml of cold water to extract glacial acetic acid, and then, freeze-dried. After the freeze-dried sponge was cut into a piece of 7 mm×7 mm×4 mm, the piece was wetted by adding dropwise about 200 gl of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed to obtain porous bone-forming grafts of the present invention.

EXAMPLE 10

A gelatin sponge (Spongel) of 7 cm×10 cm×1 cm was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain an rhBMP-2/gelatin sponge. The sponge was wetted by adding dropwise a solution prepared by adding 2.0 g of a copolymer of D,L-lactic acid and glycolic acid (molar ratio=75:25, molecular weight 50,000; made by Boehringer-Ingelheim) to 1,4-dioxane (reagent grade; made by Kanto Chemical) in which Polysorbate 80 had been added in advance to 0.1% by weight, and dissolving under heating to obtain 100 ml of the polymer solution, and then cooling to room temperature. The wetting procedure was continued until the polymer solution was no longer absorbed (about 70 ml). Then, the rhBMP-2/gelatin sponge containing the absorbed polymer solution was frozen at −30° C. and dried at the pressure of 0.1 mbar to obtain porous bone-forming grafts of the present invention.

EXAMPLE 11

A copolymer (2.0 g or 4.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Freeze-dried powder of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] prepared by a known method was added, in an amount corresponding to 20 mg to 80 mg of rhBMP-2, to the polymer solution with stirring to obtain an rhBMP-2 suspension. Thereafter, a gelatin sponge (Spongel) of 7 cm×10 cm×1 cm was wetted by adding dropwise the rhBMP-2 suspension until the rhBMP-2 suspension was no longer absorbed (about 70 ml). Then, the gelatin sponge containing absorbed rhBMP-2 suspension was frozen at −30° C., and dried at the pressure of 0.1 mbar to obtain porous bone-forming grafts of the present invention.

EXAMPLE 12

A gelatin sponge (Spongel) of 7 cm×10 cm×1 cm was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain an rhBMP-2/gelatin sponge. The sponge was wetted by adding dropwise a solution prepared by adding 2.0 g of a copolymer of D,L-lactic acid and glycolic acid (molar ratio=75:25, molecular weight=50,000; made by Boehringer-Ingelheim) to 1,4-dioxane (reagent grade; made by Kanto Chemical) in which Polysorbate 80 had been added in advance to 0.1% by weight, and dissolving under heating to obtain 100 ml of the polymer solution, and then cooling to room temperature. The wetting procedure was continued until the polymer solution was no longer absorbed (about 70 ml). Then, the rhBMP-2/gelatin sponge containing the absorbed polymer solution was frozen at −30° C. and dried at the pressure of 0.1 mbar. The dried sponge was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts ago containing rhBMP-2 [0.2 mg/ml to 1.6 mg/ml of the present invention.

EXAMPLE 13

Poly-DL-lactic acid (molecular weight=50,000; made by Mitsui Toatsu Chemicals) (1.0 g) was added to 1,4-dioxane (reagent grade; made by Kanto Chemical) in which Polysorbate 80 had been added in advance to 0.1% by weight, and dissolved therein to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 14

Poly-DL-lactic acid (molecular weight=50,000; made by Mitsui Toatsu Chemicals) (1.0 g) was added to 1,4-dioxane (reagent grade; made by Kanto Chemical) in which Polysorbate 80 had been added in advance to 1.0%, and dissolved therein to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 15

Poly-DL-lactic acid (molecular weight=60,000; made by Mitsui Toatsu Chemicals) (1.0 g) was added to 1,4-dioxane (reagent grade; made by Kanto Chemical) in which Polysorbate 80 had been added in advance to 1.0%, and dissolved therein to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 16

A copolymer (2.0 g) of D,L-lactic acid and glycolic acid (molar ratio=75:25, molecular weight=50,000; made by Boehringer-Ingelheim) was added to 1,4-dioxane (reagent grade; made by Kanto Chemical) in which Polysorbate 80 had been added in advance to 0.1% by weight, and dissolved therein to obtain 100 ml of a polymer solution. The polymer solution was cooled to room temperature. Thereafter, a collagen sponge (Helistat; made by Marion Laboratories, Inc.) of 7.5 cm×10 cm×0.3 cm was wetted by adding dropwise the polymer solution until the polymer solution was no longer absorbed. Then, the collagen sponge containing the polymer solution was frozen at −30° C., and dried at the pressure of 0.1 mbar. The freeze-dried sponge was wetted by adding dropwise about 22.5 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 17

Hyaluronic acid (molecular weight=800,000; Kibun Food Chemifa) (2.1 g) was dissolved in 300 ml of distilled water for injections. Separately, 9 g of gelatin (G-785P and G786P; made by Nitta Gelatin) was dissolved in 300 ml of a IN-acetic acid aqueous solution. The gelatin solution was added to the hyaluronic acid solution and the whole was stirred for 5 minutes at 9000 rpm in T.K. homogenizer. The generated foam was collected and frozen in a freezer of −80° C. The product was dried in a freeze-dryer to obtain a sponge.

Then, 1.0 g of poly-DL-lactic acid (molecular weight=50,000; made by Mitsui Toatsu Chemicals) was added to 1,4-dioxane (reagent grade; made by Kanto Chemical) in which Polysorbate 80 had been added in advance to 0.1% by weight, and dissolved therein to obtain 100 ml of a polymer solution. The polymer solution was cooled to room temperature. Thereafter, said sponge of 3 cm×3 cm×1 cm was wetted by adding dropwise the polymer solution until the polymer solution was no longer absorbed. Then, the sponge containing absorbed polymer solution was frozen at −30° C., and dried at the pressure of 0.1 mbar to obtain a composite porous body. The freeze-dried sponge was wetted by adding dropwise about 9 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 18

A copolymer (2.0 g) of D,L-lactic acid and glycolic acid (molar ratio=75:25, molecular weight=50,000; made by Boehringer-Ingelheim) was added to ethyl acetate (reagent grade; made by Kanto Chemical), and dissolved therein to obtain 100 ml of a polymer solution. A gelatin sponge (Spongel) of 7 cm×10 cm×1 cm was immersed in the polymer solution, and then blow-dried at room temperature to obtain a composite porous body. The dried sponge was wetted by adding dropwise about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 19

A copolymer (2.0 g) of D,L-lactic acid and glycolic acid (molar ratio=75:25, molecular weight=50,000; made by Boehringer-Ingelheim) was added to ethyl acetate (reagent grade; made by Kanto Chemical), and dissolved therein to obtain 100 ml of a polymer solution. A collagen sponge (Helistat; Marion Laboratories, Inc.) of 7.5 cm×10 cm×0.3 cm was immersed in the polymer solution, and then dried under reduced pressure at room temperature to obtain a composite porous body. The dried sponge containing absorbed polymer solution was wetted by adding dropwise about 22.5 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 20

A copolymer (2.0 g) of D,L-lactic acid and glycolic acid (molar ratio=75:25, molecular weight=50,000; made by Boehringer-Ingelheim) was added to ethyl acetate (reagent grade; made by Kanto Chemical), and dissolved therein to obtain 100 ml of a polymer solution. A collagen sponge (Helistat; Marion Laboratories, Inc.) of 7.5 cm×10 cm×0.3 cm was immersed in the polymer solution, and then blow-dried at room temperature. The dried sponge containing absorbed polymer solution was wetted by adding dropwise about 22.5 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention.

EXAMPLE 21

Poly-L-lactic acid (molecular weight=60,000; made by Boehringer-Ingelheim) (1.0 g) was added to 1,4-dioxane (reagent grade; made by Kanto Chemical) in which Polysorbate 80 had been added in advance to 0.1% by weight, and dissolved therein to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and dried at the pressure of 0.1 mbar to obtain a composite porous body. The freeze-dried sponge was wetted by adding dropwise an aqueous solution of 1% by weight of Polysorbate 80, and freeze-dried by a known method. Further, about 70 ml of a solution of rhBMP-2 [0.1 mg/ml to 0.8 mg/ml; 2.5% glycine, 0.5% sucrose, 5 mM sodium chloride, 5 mM glutamic acid, 0.01% Polysorbate 80; pH 4.5] was added dropwise to the sponge whereby the solution was absorbed, and freeze-dried by a known method to obtain porous bone-forming grafts of the present invention.

EXAMPLE 22

A copolymer (8.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, the gelatin sponge containing absorbed polymer solution was frozen at −30° C., and freeze-dried at the pressure of 0.1 mbar to obtain a composite porous body. To the freeze-dried sponge was added dropwise about 60 ml of a solution of rhBMP-2 [0.12 mg/ml to 5.9 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention containing rhBMP-2 (0.1 mg/ml to 5.0 mg/ml).

EXAMPLE 23

A copolymer (8.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.1% by weight, and dissolved under heat to obtain 100 ml of a polymer solution. The polymer solution was cooled to room temperature. To a gelatin sponge (Spongel) of 7 cm×10 cm×1 cm was added dropwise the polymer solution until the polymer solution was no longer absorbed (about 70 ml). Then, the gelatin sponge containing absorbed polymer solution was frozen at −30° C., and freeze-dried at the pressure of 0.1 mbar to obtain a composite porous body. Further, the freeze-dried sponge was cut into a piece of 7 mm×7 mm×4 mm, and then, about 170 μl of a solution prepared by mixing a solution of rhBMP-2 [1.2 mg/ml to 59 mg/ml; 2.5% glycine, 0.5% sucrose, 5 mM sodium chloride, 5 mM glutamic acid, 0.01% Polysorbate 80; pH 4.5] and blood in a ratio of 1:9 was added dropwise whereby the solution was absorbed to obtain porous bone-forming grafts of the present invention containing rhBMP-2 (0.1 mg/ml to 5.0 mg/ml).

EXAMPLE 24

A copolymer (12.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.5% by weight, and dissolved under heat to obtain 150 ml of a polymer solution. After cooling the polymer solution to room temperature, a gelatin sponge (Spongel) of 7 cm×10 cm×1 cm was immersed in the polymer solution. Then, the sponge immersed in the polymer solution was frozen at −45° C., and freeze-dried at the pressure of 0.1 mbar. The polymer attached to the surround was cut with a shaving knife and dried under heat at 135° C. for 36 minutes for sterilization. To the resulting composite porous body was added dropwise about 60 ml of a solution of rhBMP-2 [0.12 mg/ml to 5.9 mg/ml; 2.5% glycine, 0.5% sucrose, 5 mM sodium chloride, 5 mM glutamic acid, 0.01% Polysorbate 80; pH 4.5] whereby the solution was absorbed to obtain porous bone-forming grafts of the present invention containing rhBMP-2 (0.1 mg/ml to 5.0 mg/ml).

EXAMPLE 25

A copolymer (12.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.5% by weight, and dissolved under heat to obtain 150 ml of a polymer solution. After cooling the polymer solution to room temperature, a gelatin sponge (Spongel) of 7 cm×10 cm×1 cm was immersed in the polymer solution. Then, the sponge immersed in the polymer solution was frozen at −45° C., and freeze-dried at the pressure of 0.1 mbar. The polymer attached to the surround was cut with a shaving knife to obtain a composite porous body. To the resulting composite porous body was added dropwise about 60 ml of a solution of rhBMP-2 [0.12 mg/ml to 5.9 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention containing rhBMP-2 (0.1 mg/ml to 5.0 mg/ml).

EXAMPLE 26

A copolymer (10.0 g) of D,L-lactic acid and glycolic acid (molar ratio=50:50, molecular weight=40,000; made by Boehringer-Ingelheim) was added to 1,4-dioxane (reagent grade; made by Kanto Chemical) in which Polysorbate 80 had been added in advance to 0.5% by weight, and dissolved under heat to obtain 100 ml of a polymer solution. The polymer solution was cooled to room temperature. Thereafter, a gelatin sponge (Spongel) of 7 cm×10 cm×1 cm was wetted by adding dropwise the polymer solution until the polymer solution was no longer absorbed (about 70 ml). Then, it was frozen at −30° C., and freeze-dried at the pressure of 0.1 mbar to obtain a composite porous body. To the resulting material was added dropwise about 60 ml of a solution of rhBMP-2 [0.12 mg/ml to 5.9 mg/ml; 2.5% glycine, 0.5% sucrose, 5 mM sodium chloride, 5 mM glutamic acid, 0.01% Polysorbate 80; pH 4.5] whereby the solution was absorbed, and freeze-dried by a known method to obtain porous bone-forming grafts of the present invention containing rhBMP-2 (0.1 mg/ml to 5.0 mg/ml).

We claim:
1. A bone-forming graft comprising:
   (i) a composite porous body comprising:
      (1) a porous frame of a bioabsorbable hydrophilic material having a plurality of pores with continuity to one another, said pores being open to the outside, and
      (2) a surface layer of a bioabsorbable polymer material, and
   (ii) a bone morphogenetic factor carried on said composite porous body.

2. A bone-forming graft according to claim 1, wherein said bioabsorbable hydrophilic material is one or more compounds selected from a group consisting of gelatin, hyaluronic acid, a hyaluronic acid derivative, collagen, a collagen derivative, chitosan, a chitosan derivative, and triethanolamine alginate, and said bioabsorbable polymeric material is one or more compounds selected from a group consisting of a polylactic acid, a copolymer of a polylactic acid and a polyglycolic acid, and a copolymer of poly[bis(p-carboxyphenoxy)propane]anhydride and sebacic acid.

3. A bone-forming graft according to claim 2, wherein said bioabsorbable hydrophilic material is one or more compounds selected from a group consisting of gelatin, collagen, and a polyion complex of gelatin and hyaluronic acid.

4. A bone-forming graft according to claim 2 or 3, wherein said bioabsorbable polymer material is one or more compounds selected from a group consisting of a polylactic acid having an average molecular weight of 5,000 to 1,500,000, and a copolymer of a polylactic acid and a polyglycolic acid having an average molecular weight of 5,000 to 1,500,000 and a polylactic acid content(molar ratio) of not less than 40%.

5. A bone-forming graft according to claim 1, wherein a surfactant is applied on a surface of said composite porous body.

6. A bone-forming graft according to claim 1, wherein said composite porous body has an average pore size of 10 to 1000 μm and a porosity of not less than 60%.

7. A bone-forming graft according to claim 6, wherein said composite porous body has an average pore size of 40 to 600 μm and a porosity of not less than 80%.

8. A bone-forming graft according to claim 3 or 7, wherein said porous frame of a bioabsorbable hydrophilic material is a gelatin sponge having an average pore size of 50 to 500 μm and a porosity of not less than 90%.

9. A composite porous body comprising a bioabsorbable hydrophilic material which is one or more compounds selected from a group consisting of gelatin, hyaluronic acid, and a hyaluronic acid derivative, and a surface layer of a bioabsorbable polymer material which is one or more compounds selected from a group consisting of a polylactic acid, a copolymer of a polylactic acid and a polyglycolic acid, and a copolymer of poly[bis(p-carboxyphenoxy)propane]anhydride and sebacic acid.

10. A composite porous body according to claim 9, wherein said bioabsorbable hydrophilic material is one or more compounds selected from a group consisting of gelatin, and a polyion complex of gelatin and hyaluronic acid.

11. A composite porous body according to claim 9 or 10, wherein said bioabsorbable polymer material is one or more compounds selected from a group consisting of a polylactic acid having an average molecular weight of 5,000 to 1,500,000, and a copolymer of a polylactic acid and a polyglycolic acid having an average molecular weight of 5,000 to 1,500,000 and a polylactic acid content (molar ratio) of not less than 40%.

12. A composite porous body according to claim 11, wherein said porous frame of a bioabsorbable hydrophilic material is a gelatin sponge having an average pore size of 50 to 500 μm and a porosity of not less than 90%.

13. A composite porous body according to claim 9, wherein a surfactant is applied on a surface of said composite porous body.

* * * * *